United States Patent [19]

Bohm

[11] 4,028,929

[45] June 14, 1977

[54] MODIFIED UBBELOHDE VISCOSIMETER

[75] Inventor: Ludwig Böhm, Mainz, Germany

[73] Assignee: Hoechst Aktiengesellschaft, Frankfurt am Main, Germany

[22] Filed: Mar. 5, 1976

[21] Appl. No.: 664,255

[30] Foreign Application Priority Data

Mar. 7, 1975   Germany ............................ 2509916

[52] U.S. Cl. .................................................. 73/55
[51] Int. Cl.² ........................................ G01N 11/06
[58] Field of Search ........................................ 73/55

[56] References Cited

UNITED STATES PATENTS

| | | | |
|---|---|---|---|
| 2,095,324 | 10/1937 | Fitzsimons | 73/55 |
| 3,071,961 | 1/1963 | Heigl et al. | 73/55 |
| 3,559,463 | 2/1971 | Tovrog et al. | 73/55 |
| 3,699,804 | 10/1972 | Gassmann et al. | 73/55 |

OTHER PUBLICATIONS

*Semimicro Dilution Viscometer* in NBS Technical News Bulletin, pp. 158–159, Nov. 1955.

Primary Examiner—Richard C. Queisser
Assistant Examiner—Joseph W. Roskos
Attorney, Agent, or Firm—Curtis, Morris & Safford

[57] ABSTRACT

A Ubbelohde viscosimeter is disclosed which is modified according to the present invention by mounting to its reservoir a pressure tube and to the upper ends of the pressure tube and the conventional capillary tube a double three way cock. The cock controls pressure supply to the reservoir, as well as selectively connecting the reservoir to atmosphere. In addition a separate suction tube is provided in association with the reservoir to permit selective withdrawal of material from the reservoir. By this arrangement viscosity measurements of polymer solutions at high temperatures are possible without removing the viscosimeter from the thermostat for cleaning.

1 Claim, 4 Drawing Figures

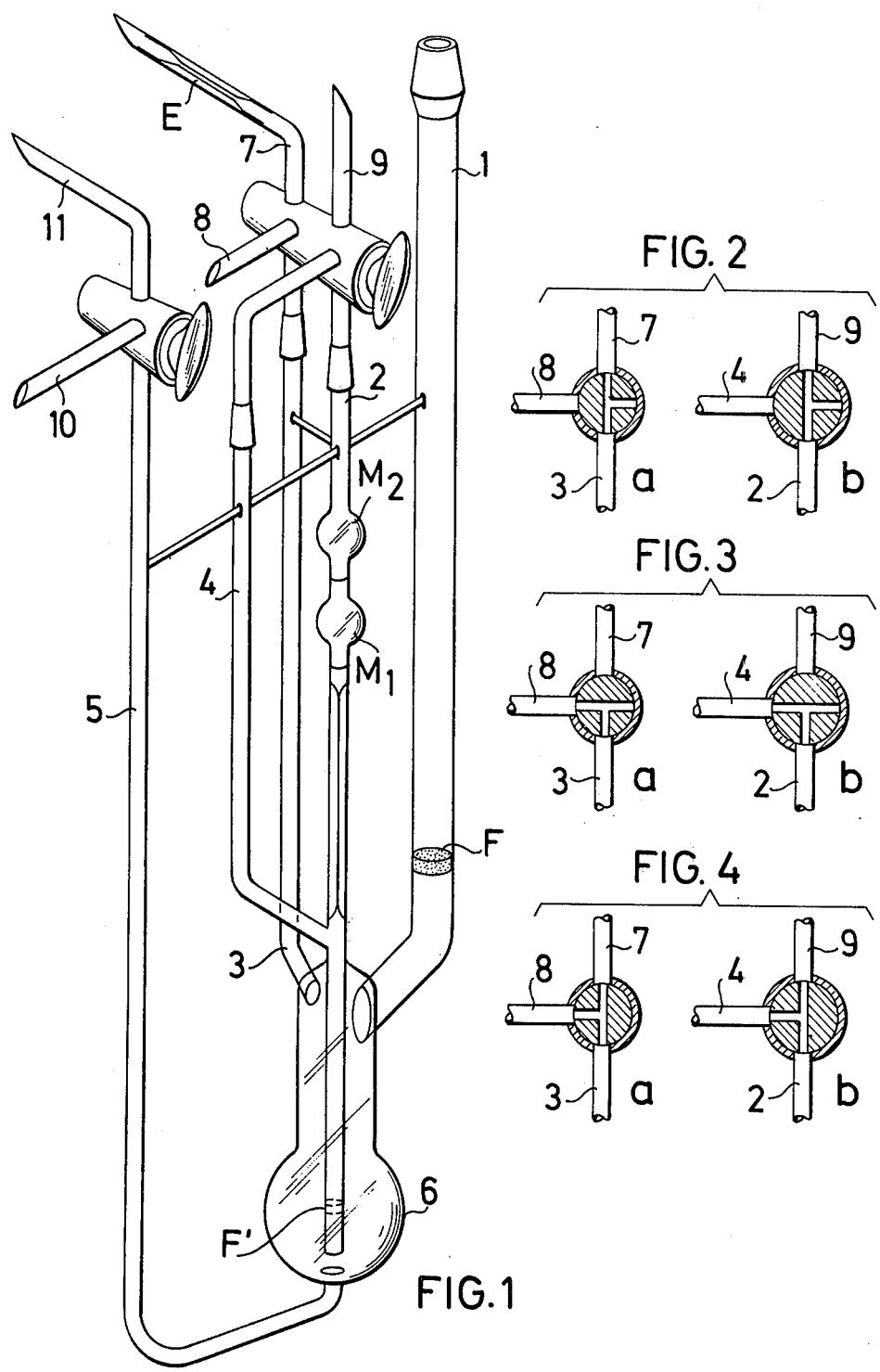

MODIFIED UBBELOHDE VISCOSIMETER

The present invention relates to an improvement in or modification of the Ubbelohde viscosimeter.

For measuring the viscosity of solvents and solutions numerous capillary viscosimeters of different constructions have been proposed. The best known viscosimeters of this type are the Ostwald viscosimeter (cf. G. V. Schulz, H. J. Cantow, Viscosimetrische Methode, in Houben-Weyl "Methoden der Organishen Chemie", volume 3, page 431 (1955)), the Cannon-Fenske-Ubbelohde viscosimeter and the Atlantic viscosimeter (ASTM Designation D 445-61). In these viscosimeters the time required for a definite volume to flow through a standard capillary is measured. In the case of the Ubbelohde viscosimeter (cf. L. Ubbelohde, J. Inst, Petrol., volume 19, page 376 (1933) and volume 22, page 37 (1936)) the volume of the sample introduced into the viscosimeter need not be defined exactly. In the viscosimeter a solution could be further diluted by adding additional quantities of solvent and in this manner measurements of concentration series can be carried out in simple manner, which is required for determining the Staudinger indices of polymer solutions (cf. DIN 53 728).

In general, the known capillary viscosimeters have the drawback that they must be removed from the thermostat for cleaning and preparing the next measurement. Only the viscosimeter specified by the American Society for Testing and Materials (ASTM Designation D 1601-61) may remain in the thermostat. In this device a suction tube is inserted in the viscosimeter with which the contents are withdrawn.

The present invention relates to an improvement in or modification of the Ubbelohde viscosimeter in the form modified by Fitzsimons and comprising a capillary tube with defined diameter, an upper bulb, a measuring bulb, a large side tube, a compensating tube and a reservoir. According to the invention the reservoir is additionally provided with a tube to apply pressure to the reservoir so that the liquid, the viscosity of which is to be measured, can be pressed through the capillary into the measuring bulb and the upper bulb, and with a further tube having a small internal diameter to suck off the liquid from the reservoir and the various tubes are interconnected by means of a double three-way cock, with the aid or which cock the measuring procedure is initiated.

The viscosimeter of the invention allows of measuring in a simple and rapid manner the viscosity of solutions and solvents, without removal of the viscosimeter from the thermostat for cleaning and preparing the next measurement being necessary. This is especially advantageous for measurements at elevated temperature. Owing to the double three-way cock measurement under a protective gas may also be carried out in very simple manner.

The invention will now be described in further detail with reference to the accompanying drawing in which FIG. 1 is front view of an Ubbelohde viscosimeter as modified by Fitzsimons (cf. Ind. Eng. Chem. Anal. Ed. 7 (1935) page 345 with the modifications according to the invention and FIGS. 2 to 4 illustrate different positions of the double three-way cock.

The viscosimeter consists of a tube 2 with capillary having a defined diameter and measuring bulb $M_1$ and upper bulb $M_2$, a side tube 4 and the reservoir 6. The reservoir is provided with a lateral tube 1 through which the sample to be measured is introduced. In the tube a glass frit F is included by melting and the upper end of the tube is closed by a cap. Instead of the frit a sintered glass filter as used in the viscosimeter described by the American Society for Testing and materials may be inserted in the tube. Alternatively, the frit may be melted in the lower end of tube 2 as indicated by reference F', for example as used with the viscosimeter described by the German Standards Institution (cf. DIN 53 728). At the bottom of reservoir 6 a tube 5 having a small inner diameter is provided for through which the contents of the reservoir can be drawn off.

At the upper end tube 5 carries a three-way cock with tubes 10 and 11 through which the liquid is removed from the viscosimeter and tube 5 is aerated. Pressure tube 3 and capillary tube 2 carry at their upper end a double three-way cock by means of which tube 2 can be connected with the atmosphere over short pipe 9 or with compensating tube 4 and reservoir 6 can be connected with a pressure source (not shown) via short pipe 7 with capillary E or communicate with the atmosphere by means of short pipe 8. Pipes 8, 9 and 11 may also be connected with the souce of a protective gas (not shown).

When the three-way cock is in the position shown in FIG. 2 pressure is applied to the reservoir 6 through tube 7 connected with a pressure source. For this purpose a protective gas such as nitrogen or argon could be used. The liquid to be tested is now pushed through the capillary into measuring bulb $M_1$ and upper bulb $M_2$. As soon as the bulbs are filled the cock is turned into the position according to FIG. 3 whereby tubes 2 and 4 are connected with each other, while the pressure source is closed. Now the liquid does not rise further in tubes 2 and 4. When the cock is then turned into the position represented in FIG. 4, the pressure in the system is released and the liquid in tube 4 rapidly flows back into the reservoir 6. The time to drain the liquid through the capillary can now be determined.

After the measurement the liquid is withdrawn through tube 5. Next, the viscosimeter is repeatedly washed by introducing into tube 1 a solvent heated to the measuring temperature. The washing liquid is removed through tube 5. To dry the viscosimeter air is sucked through. Before the next sample is introduced into the viscosimeter, it may be flushed with a protecting gas introduced through pipe 7.

The dimensions of the capillaries and the measuring bulb $M_1$ chosen in accordance with the indications in literature in a manner such that the corrections to be considered and systematic errors will be as small as possible (cf. G. V. Schulz, H. J. Cantow, Makromol. Chem. volume 13, page 71 (1954) and DIN 53 012).

As compared to known viscosimeters, the improved viscosimeter of the invention has all advantages of an Ubbelohde viscosimeter, that is to say the liquid or solution need not be introduced by a pipet and concentration series can be measured within a short period of time, and, moreover, for cleaning and preparing the viscosimeter for the next measurement it can remain in the thermostat without any manipulation on the viscosimeter itself being necessary. This face is especially advantageous when the measurements are carried out at elevated temperature, for example when the viscosities of poly-olefin solutions in decahydronaphthalene are measured. Owing to its easy handling the viscosimeter of the invention is especially suitable for series measurements.

What is claimed is:

1. In a viscosimeter including a reservoir, a side tube connected in communication with the reservoir and having an upper end portion for introducing liquid to be measured into the reservoir; a hollow capillary tube communicating with said reservoir including a lower end within the reservoir near its bottom and an upper end above the reservoir; said capillary tube including a measuring bulb and a separate upper bulb therein between said reservoir and said upper end thereof; and a pressure compensating tube having a lower end communicating with said capillary tube near the top of the reservoir and an upper end communicating with the capillary tube near the upper end thereof; wherein the improvement comprises a separate pressure tube having a lower end communicating with said reservoir near its upper end and extending upwardly therefrom adjacent said capillary tube; and a double three-way cock valve connected to the upper ends of said pressure tube and said capillary tube at its connection with the upper end of said compensating tube and having three short tubes secured thereto, one aligned with the upper end of the capillary tube, one aligned with the upper end of the pressure tube and one in the plane of the pressure tube extending at an angle thereto; said double three way cock valve having two separate port arrays therein respectively associated with $i$) said capillary tube, the short tube associated therewith and the pressure compensating tube and $ii$) the pressure tube and the two other short tubes; to selectively control fluid and gas flow therethrough; and a suction tube connected at one end to the bottom of the reservoir and including, at its other end, a separate three-way cock valve having two short tubes extending therefrom.

* * * * *